US00PP36351P2

(12) United States Plant Patent
Hachmann

(10) Patent No.: US PP36,351 P2
(45) Date of Patent: Dec. 31, 2024

(54) ***DASIPHORA* PLANT NAMED 'HACHAPP'**

(50) Latin Name: ***Dasiphora fruticosa* subsp. *fruiticosa***
Varietal Denomination: Hachapp

(71) Applicant: Holger Hachmann, Barmstedt (DE)

(72) Inventor: Holger Hachmann, Barmstedt (DE)

(73) Assignee: H. HACHMANN INH. HOLGER HACHMANN, Barmstedt (DE)

( * ) Notice: Subject to any disclaimer, the term of this patent is extended or adjusted under 35 U.S.C. 154(b) by 0 days.

(21) Appl. No.: 18/637,515

(22) Filed: Apr. 17, 2024

Related U.S. Application Data

(60) Provisional application No. 63/460,508, filed on Apr. 19, 2023.

(51) Int. Cl.
*A01H 5/02* (2018.01)
*A01H 6/74* (2018.01)

(52) U.S. Cl.
USPC ..... Plt./237

(58) Field of Classification Search
USPC ..... Plt./226, 237
See application file for complete search history.

(56) References Cited

U.S. PATENT DOCUMENTS

PP9,874 P * 4/1997 Lenz ..... Plt./237

* cited by examiner

*Primary Examiner* — Karen M Redden
(74) *Attorney, Agent, or Firm* — Penny J. Aguirre

(57) ABSTRACT

A new cultivar of *Dasiphora* plant named 'Hachapp' that is characterized by its compact plant habit, its flattened globular to globular plant shape, and its flowers that are salmon pink in color with yellow centers and fade very little in color after opening.

2 Drawing Sheets

Botanical classification: *Dasiphora fruticosa* subsp. *fruiticosa.*

Variety denomination: 'Hachapp'.

CROSS REFERENCE TO RELATED APPLICATIONS

This application is related to a European Community Plant Variety Office (CPVO) Plant Breeder's Rights Application filed on Jul. 12, 2018, application No. 2018/3255. This application claims priority to a U.S. Provisional Patent Application, Application No. 63/460,508, filed Apr. 19, 2023 under 35 U.S.C. 119(e), the entire contents of which is incorporated by reference herein. This application is co-pending with a U.S. Plant Patent Application filed for a plant derived from the same breeding program that is entitled *Dasiphora* Plant Named 'Hachrosa' (U.S. Plant patent application Ser. No. 18/637,530)*.

* (Applicant gives the examiner the authority to replace the U.S. Plant Patent Application No. with a Patent No. if applicable and delete this statement.)

BACKGROUND OF THE INVENTION

The present invention relates to a new and distinct cultivar of *Dasiphora fruticosa* subsp. *fruiticosa* (syn. *Dasiphora fruticosa*, syn. *Potentilla fruticosa*). The new cultivar will be referred to hereafter by its cultivar name, 'Hachapp'. 'Hachapp' is a new cultivar of deciduous shrub grown for landscape use.

The Inventor discovered the new cultivar in summer of 2016 as a seedling that was discovered growing in a trial field plot that was planted with many varieties and unnamed plants of *Dasiphora fruticosa* subsp. *fruiticosa* in Barmstedt, Germany. Both the female and male parent are unknown.

Asexual propagation of the new cultivar was first accomplished by softwood cuttings by the Inventor in Barmstedt, Germany in August of 2016. Asexual propagation by softwood cuttings has determined that the characteristics of the new cultivar are stable and reproduced true to type in successive generations.

SUMMARY OF THE INVENTION

The following traits have been repeatedly observed and represent the characteristics of the new shrub rose. These attributes in combination distinguish 'Hachapp' as a unique cultivar of *Dasiphora.*

1. 'Hachapp' exhibits a compact plant habit.
2. 'Hachapp' exhibits a flattened globular to globular plant shape.
3. 'Hachapp' exhibits flowers that are salmon pink in color with yellow centers and fade very little in color after opening.

'Hachapp' is unique from all of the plants of *Dasiphora fruticosa* subsp. *fruiticosa* that were growing in the field plot where the new cultivar was discovered. 'Hachapp' can be most closely compared to the *Dasiphora fruticosa* subsp. *fruiticosa* cultivars 'Daydawn' (not patented), 'Pink Beauty' (not patented) and 'Hachrosa'. All three are similar to 'Hachapp' in having flowers that are pinkish in color. 'Daydawn' differs from 'Hachapp' in having a less compact plant habit, a less globular plant shape, and flowers that are lighter in color. 'Pink Beauty' differs from 'Hachapp' in having a less compact plant habit, a less globular plant shape, and flowers that are pink in color. 'Hachrosa' differs from 'Hachapp' in having flowers that are lilac pink in color with red-pink centers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Monrovia, Pahls, Bigboyplants, lgmag, garden center marketing, trees today nursery, hubspotusercontent20, landscape business, gpnmag, issuu, Logan greenhouse, kapias, Cascadian Nurseries, giecdn, and scribd.

BRIEF DESCRIPTION OF THE DRAWINGS

The accompanying color photographs illustrate the overall appearance and distinct characteristics of the new *Dasiphora*. The photographs were taken of a 1.5-year-old plant as grown outdoors in a 1.5-liter container at a nursery in Barmstedt, Germany.

The photograph in FIG. 1 provides a view of a plant of 'Hachapp' in bloom.

Figure 1:
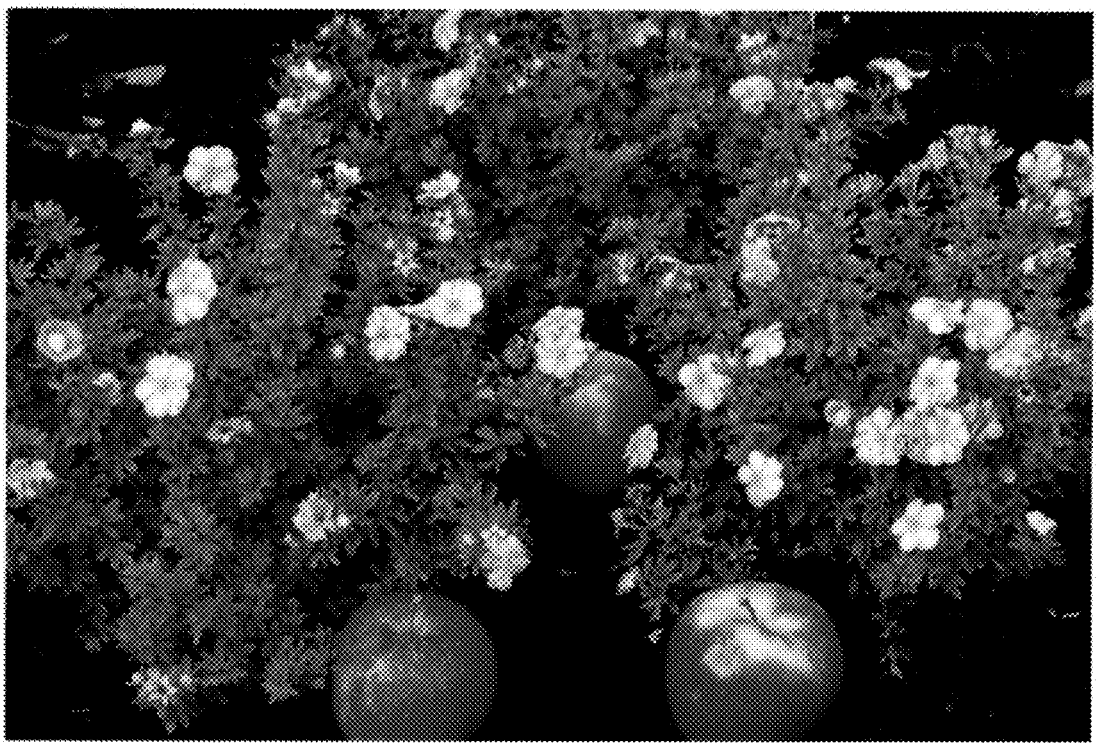
Figure 2:
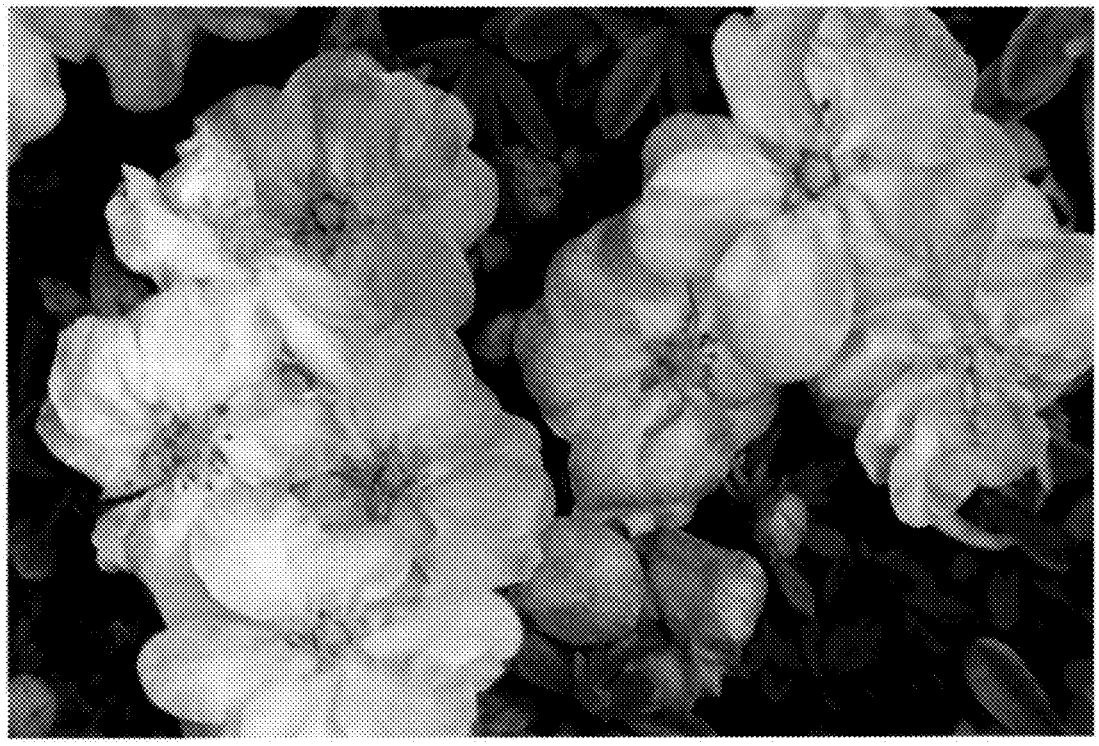

The photograph in FIG. 2 provides a close-up view of the flowers of 'Hachapp'.

The colors in the photographs are as close as possible with the photographic and printing technology utilized and the color values cited in the detailed botanical description accurately describe the colors of the new *Dasiphora*.

DETAILED BOTANICAL DESCRIPTION

The following is a description of 1-year-old plants as grown outdoors in 9-cm containers in Boskoop, The Netherlands. The phenotype of the new cultivar may vary with variations in environmental, climatic, and cultural conditions, as it has not been tested under all possible environmental conditions. The color determination is in accordance with The 2019 Colour Chart of The Royal Horticultural Society, London, England, except where general color terms of ordinary dictionary significance are used.

General description:

*Blooming period*.—May into July in Germany.

*Plant type*.—Deciduous shrub.

*Plant habit*.—Broadly spreading and upright, globular to flatten globular.

*Height and spread*.—An average of 17.8 cm in height and 19.3 cm in spread as a 1-year-old plant as grown in a container and an average of 60 cm in height and 70 cm in width as a mature plant grown in the landscape.

*Hardiness*.—At least in U.S.D.A. Zones 3 to 8.

*Diseases and pests*.—Low susceptibility to powdery mildew has been observed in Germany (caused by *Podosphaera* sp. and other unknown causative agents), no susceptibility or resistance to pests has been observed).

*Propagation*.—Softwood cuttings.

*Root description*.—Fibrous.

*Growth rate*.—Low to moderate.

*Root development*.—Cuttings initiate roots in 6 to 8 weeks and a fully rooted cutting plant is produced in 10 months.

Branch description:

*Branch shape*.—Rounded.

*Branch color*.—Young; 145C, mature; 164A to 164B.

*Branch surface texture*.—Moderately pubescent; covered with short soft hairs an average of 0.5 mm in length and NN155D in color, older bark exfoliating in small strips.

*Branching*.—Freely branching.

*Branch size*.—An average of 10.7 cm in length and 1 mm in diameter.

*Branch quantity*.—Main; 4, lateral; 12.

*Internode length*.—Average of 6.5 mm.

Foliage description:

*Leaves*.—Compound, alternate arrangement, flat to slightly carinate in aspect, reniform in shape, an average of 1.25 cm in length, 1.65 cm in width, 17 leaves per branch, leaf venation is pinnate.

*Leaflets*.—5, occasionally 3, elliptic in shape, acute apex and base, entire margins, an average of 1 cm in length and 3.5 mm in width, unlobed, both surfaces matte, upper surface sparsely to moderately pubescent, lower surface moderately pubescent, hairs are soft, 0.5 mm in length, NN155D in color, color; young upper surface a blend of 143B and 143C, young lower surface 138B, mature upper surface 137B, veins 137B, mature lower surface 138B, veins 146C.

*Stipules*.—Ovate in shape, both sides smooth and glabrous, matte, 6 mm in length, 2.5 mm in width, top narrow acute, base narrow cuneate, color both surfaces; N199D, veined 200D.

*Petioles*.—An average of 4 mm in length and 0.75 mm in diameter, medium to high strength, color; upper surface 144B, lower surface 146D, surface is moderately pubescent short hairs 0.75 mm in length, NN155D in color.

Inflorescence description:

*Inflorescence type*.—Solitary, terminal and axillary at upper nodes of stems.

*Flower number*.—An average of 2 per main stem, 5 flowers and buds per plant.

*Flower fragrance*.—None.

*Flower longevity*.—About 5 days, self-cleaning.

*Flower type*.—Single, rotate.

*Flower aspect*.—Upright to outward.

*Flower size*.—An average of 2.7 cm in diameter and 7 mm in depth.

*Pedicels*.—An average of 3 mm in length, 1 mm in diameter, held in a 7.5° angle, 138C in color, surface is matte, and is densely covered with soft, short hairs, average of 0.5 mm in length, N155A in color.

*Flower buds*.—Nearly spherical in shape, an average of 5 mm in length, 5.5 mm in diameter, 150B to 150C in color, surface is smooth, sparsely to moderately pubescent with soft, short hairs, 1.5 mm in length, N155A in color.

*Sepals*.—5, placed in one whorl, deltoid in shape, entire margins, 5.5 mm in length, 4 mm in width, broadly cuneate base, acute apex, upper surface smooth and glabrous, lower surface moderately pubescent with short hairs, 1 mm in length, too small to measure color, color; when opening and fully open upper surface 150B, margins and tips 151A, when opening and fully open lower surface 150B to 150C.

*Petals.*—6, varying between 5 to 8, 1 whorl, broadly ovate to nearly orbicular in shape, obtuse apex, cuneate base, margins are entire and slightly undulate, both surfaces are smooth, glabrous, and matte, color; when opening upper surface 35C, base 5B to 5C, when opening lower surface 11D, margins 36A to 36B, base 5D, when fully open upper surface 16D, margins 35C, base 5C, when fully open lower surface 11D, margins 36A to 36B, base 5D.

*Calyx.*—Rotate, 1.5 mm in length, 15 cm in diameter.

Reproductive organs:

*Pistils.*—Average of 60, 1 mm in length, stigma; club-shaped, 0.2 mm in length, diameter, 153D in color, style; 0.8 mm in length, 5C in color, ovary; 143C in color.

*Stamens.*—30 per flower, filaments; average of 1 mm in length, 154C in color, anthers; average of 1 mm in length and 0.75 mm in width, short oblong in shape, 12A in color, pollen; low in quantity, 12C in color.

*Fruit and seed.*—Have not been observed to date.

It is claimed:

1. A new and distinct cultivar of *Dasiphora* plant named 'Hachapp' as herein illustrated and described.

* * * * *